(12) United States Patent
Zhang et al.

(10) Patent No.: US 11,741,357 B2
(45) Date of Patent: *Aug. 29, 2023

(54) GATHERING DATA IN A COMMUNICATION SYSTEM

(71) Applicant: Microsoft Technology Licensing, LLC, Redmond, WA (US)

(72) Inventors: Cheng Zhang, Cambridge (GB); Reinhard Sebastian Bernhard Nowozin, Cambridge (GB); Ameera Patel, Cambridge (GB); Danielle Charlotte Mary Belgrave, Cambridge (GB); Konstantina Palla, London (GB); Anja Thieme, Cambridge (GB); Iain Edward Buchan, Cambridge (GB); Chao Ma, Cambridge (GB); Sebastian Tschiatschek, Cambridge (GB); Jose Miguel Hernandez Lobato, Cambridge (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 873 days.

This patent is subject to a terminal disclaimer.

(21) Appl. No.: 16/443,788

(22) Filed: Jun. 17, 2019

(65) Prior Publication Data

US 2020/0104702 A1    Apr. 2, 2020

(30) Foreign Application Priority Data

Sep. 27, 2018 (GB) ..................... 1815765

(51) Int. Cl.
*G06N 3/08* (2023.01)
*G06F 16/332* (2019.01)

(52) U.S. Cl.
CPC .......... *G06N 3/08* (2013.01); *G06F 16/3329* (2019.01)

(58) Field of Classification Search
CPC .............................. G06N 3/08; G06F 16/3329
See application file for complete search history.

(56) References Cited

U.S. PATENT DOCUMENTS

| 6,526,395 B1 | 2/2003 | Morris |
| 7,392,185 B2 | 6/2008 | Bennett |

(Continued)

FOREIGN PATENT DOCUMENTS

CA    2846919 A1    9/2014

OTHER PUBLICATIONS

"International Search Report and Written Opinion Issued in PCT Application No. PCT/US2019/048681", dated Dec. 10, 2019, 10 Pages.

(Continued)

*Primary Examiner* — Sang H Kim
(74) *Attorney, Agent, or Firm* — Barta, Jones & Foley, PLLC

(57) ABSTRACT

A computer-implemented method comprising: outputting questions to a user via one or more user devices, and receiving back responses to some of the questions from the user via one or more user devices; over time, controlling the outputting of the questions so as to output the questions under circumstances of different values for each of one or more items of metadata, wherein the one or more items of metadata comprise one or more physical conditions of the user; monitoring whether or not the user responds when the question is output with the different metadata values; training the machine learning algorithm to learn a value of each of the items of metadata which optimizes a reward function, (Continued)

and based thereon selecting a circumstance when the user is exhibiting a particular physical condition to output subsequent questions.

20 Claims, 7 Drawing Sheets

(56) References Cited

U.S. PATENT DOCUMENTS

| | | | |
|---|---|---|---|
| 8,284,985 | B2 | 10/2012 | Charpentier |
| 9,444,772 | B2 | 9/2016 | Ventilla et al. |
| 10,755,294 | B1 | 8/2020 | Podgomy et al. |
| 11,217,033 | B1 | 1/2022 | Morgan et al. |
| 2003/0182117 | A1 | 9/2003 | Monchi et al. |
| 2006/0282306 | A1 | 12/2006 | Thissen-Roe |
| 2013/0297553 | A1 | 11/2013 | Biemer |
| 2013/0346496 | A1 | 12/2013 | Maarek et al. |
| 2014/0188901 | A1 | 7/2014 | Grauman et al. |
| 2014/0272914 | A1* | 9/2014 | Baraniuk ............ G09B 7/00 434/362 |
| 2016/0210442 | A1 | 7/2016 | Ethington et al. |
| 2016/0239738 | A1 | 8/2016 | Feng et al. |
| 2017/0103179 | A1 | 4/2017 | Jiao et al. |
| 2017/0262609 | A1* | 9/2017 | Perlroth ............. G16H 10/60 |
| 2017/0300648 | A1 | 10/2017 | Charlap |
| 2017/0351962 | A1 | 12/2017 | Appel et al. |
| 2017/0372215 | A1 | 12/2017 | Platt et al. |
| 2018/0046773 | A1* | 2/2018 | Tang ................. G16H 40/20 |
| 2018/0122509 | A1 | 5/2018 | Christiansson |
| 2018/0137433 | A1* | 5/2018 | Devarakonda ........ G06N 5/022 |
| 2018/0330802 | A1 | 11/2018 | Sharifi Sedeh et al. |
| 2019/0043623 | A1 | 2/2019 | Watlington, IV |
| 2019/0083031 | A1 | 3/2019 | Hanina et al. |
| 2019/0130248 | A1* | 5/2019 | Zhong ................. G06N 5/04 |
| 2019/0335006 | A1* | 10/2019 | George ............ G06N 3/0454 |
| 2020/0105381 | A1 | 4/2020 | Zhang et al. |
| 2021/0366618 | A1* | 11/2021 | Schoedl ............. G16H 50/30 |

OTHER PUBLICATIONS

"How has Machine Learning Been Applied to Healthcare?", Retrieved From: https://www.quora.com/How-has-machine-learning-been-applied-to-healthcare, Retrieved Date: Jan. 12, 2018, 6 Pages.

Johansson, Pontus, "NLP Techniques for Adaptive Dialogue Systems", Retrieved From: https://pdfs.semanticscholar.org/6dfa/fd732d9e2898e204046832e1a6c1408bdb51.pdf?_ga=2.266963782.992861717.1561008239-416408486.1554100465, Jan. 2002, 12 Pages.

Lewenberg, et al., "Knowing What to Ask: A Bayesian Active Learning Approach to the Surveying Problem", In Proceedings of the Thirty-First AAAI Conference on Artificial Intelligence, Feb. 12, 2017, 11 Pages.

Loisel, et al., "Modeling Human Interaction to Design a Human-Computer Dialog System", In Journal of Computing Research Repository, Nov. 2009, 6 Pages.

Rajpurkar, et al., "Malaria Likelihood Prediction by Effectively Surveying Households Using Deep Reinforcement Learning", In Journal of Computing Research Repository, Nov. 2017, 7 Pages.

"International Search Report and Written Opinion Issued in PCT Application No. PCT/US19/038868", dated Sep. 10, 2019, 11 Pages.

"Non Final Office Action Issued in U.S. Appl. No. 16/443,734", dated Mar. 4, 2022, 25 Pages.

"Final Office Action Issued in U.S. Appl. No. 16/443,734", dated Jun. 24, 2022, 27 Pages.

"Non Final Office Action Issued in U.S. Appl. No. 16/443,734", dated Oct. 20, 2022, 17 Pages.

"Notice of Allowance Issued in U.S. Appl. No. 16/443,734", dated Feb. 2, 2023, 11 Pages.

Sun, et al., "Conversational Recommender System", In Proceedings of the 41st International ACM SIGIR Conference on Research & Development in Information, Jul. 8, 2018, pp. 235-244.

"Notice of Allowance Issued in U.S. Appl. No. 16/443,734", dated Mar. 23, 2023, 6 Pages.

* cited by examiner (a) Inference model (b) Generative model (a)

(b)

(c)

(d)

(e)

(f)

(g)

(h)

GATHERING DATA IN A COMMUNICATION SYSTEM

CROSS-REFERENCE TO RELATED APPLICATION

This non-provisional utility application claims priority to UK patent application number 1815765.1 entitled "GATHERING DATA IN A COMMUNICATION SYSTEM" and filed on Sep. 27, 2018, which is incorporated herein in its entirety by reference.

BACKGROUND

Questionnaires are widely used to monitor conditions and experiences. Health, marketing, management, government and many other sectors use questionnaires to measure human factors such as attitudes, expectations, intentions and experiences. These sectors are saddled with a legacy of questionnaires designed for infrequent, paper-based use.

Clinics are now translating questionnaires into mobile apps, attempting to detect the changes over time in conditions that could trigger prompt interventions (by the patient or healthcare provider) preventing deterioration, improving outcomes and reducing care-costs. It is also possible to provide multi-channel administration of questionnaires, through a combination of modalities such as app, chat-bot and/or voice user interfaces.

SUMMARY

Advances in user interfaces such as apps, chat bots and voice user interfaces, combined with machine learning, offer opportunities to rethink the questionnaire in order to improve surveying or monitoring. Such technology provides the ability to switch from a "latitudinal" or "vertical" approach to questionnaires, where a user is asked in a single session to complete the whole questionnaire/survey, to a "longitudinal" or "horizontal" approach, whereby the user can be asked questions spread out over the course of the day, week, etc. This can fit in better with the user's life and thus elicit a more informative data stream.

While the questions in a questionnaire or survey may relate to a human experience, there is also a technical challenge in trying to elicit more information from the user, e.g. to achieve greater accuracy in the results of the questionnaire or to improve the efficiency of the questionnaire. By eliciting more information from the user the results better represent the experience or condition of the user that is being measured. For instance, consider the case where user responses are employed to predict the state of a condition of the user, such as a disease or other health condition (e.g. the prediction taking the form of a combined score based on the responses to multiple questions). While the questions may relate to a subjective experience of the user, there is also an objective result in terms of a prediction, e.g. the onset of a health problem such as an asthma attack, which may ultimately be judged objectively correct or incorrect or to have a certain likelihood of being correct (e.g. based on statistical data for multiple users). The more information (e.g. the more responses) that can be obtained, the more accurate the result will tend to be. It would therefore be desirable to increase the number of available responses from the user or the amount of information gained from asking a question.

According to one aspect disclosed herein, there is provided computing apparatus comprising one or more processors and storage storing code arranged to run on the one or more processors, wherein the code is configured so as when run to perform operations of: outputting questions to a user via one or more user devices, and receiving back responses to some of the questions from the user via one or more user devices; over time, controlling the outputting of the questions so as to output the questions under circumstances of different values for each of one or more items of metadata, wherein the one or more items of metadata comprise one or more physical conditions of the user; monitoring whether or not the user responds when the question is output with the different metadata values; supplying the metadata values and a corresponding indication of whether the user responded as training inputs to a machine learning algorithm; training the machine learning algorithm to learn a value of each of the one or more items of metadata which optimizes a reward function, and based thereon selecting a circumstance when the user is exhibiting a particular physical condition to output one or more subsequent questions.

In embodiments the apparatus may further comprise features in accordance with any embodiment disclosed herein.

Said apparatus may be implemented (at least in part) on a server comprising a network interface for communicating with the one or more user devices via a network. In this case the code run on the one or more processors of the server is configured to use said network interface to control the one or more user devices to perform said outputting to the user and said receiving of the responses via the user devices. Alternatively it is not excluded that the apparatus may be implemented partially or wholly on one or more of the user devices.

According to further aspects, there may be provided a corresponding method and computer program product for performing any of the operations attributed to the apparatus or system according to any embodiment disclosed herein.

Additionally, to improve the user's experience, the questions may be asked dynamically based on the previous personalized answer. In this way, the system is able to obtain the maximum information about the user's health status with the minimum number of questions. An adaptive questionnaire will save the time of the user, as well as improve the user's experience.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Nor is the claimed subject matter limited to implementations that solve any or all of the disadvantages noted herein.

BRIEF DESCRIPTION OF THE DRAWINGS

To assist understanding of the present disclosure and to show how embodiments may be put into effect, reference is made, by way of example only, to the accompanying drawings in which.

DETAILED DESCRIPTION OF EMBODIMENTS

Figure 1:
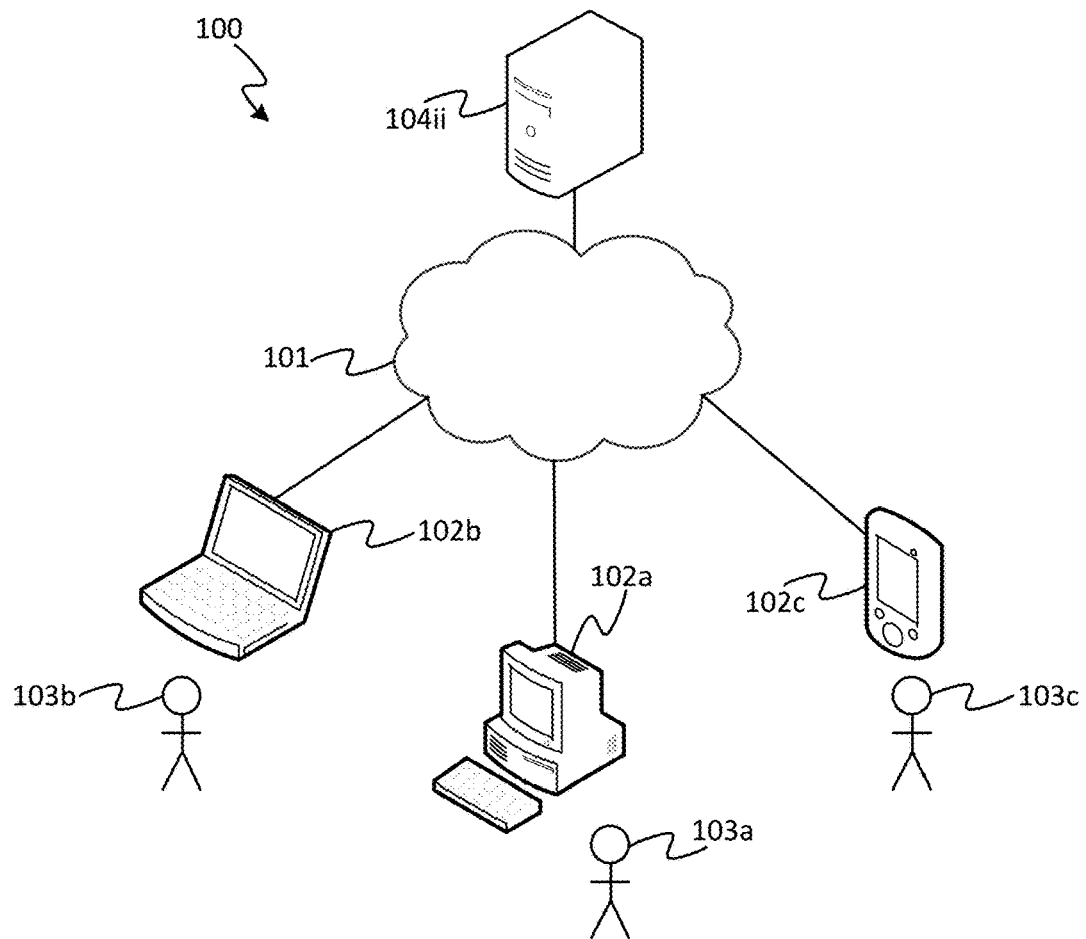
FIG. 1 is a schematic illustration of an example communication system.
Figure 1:
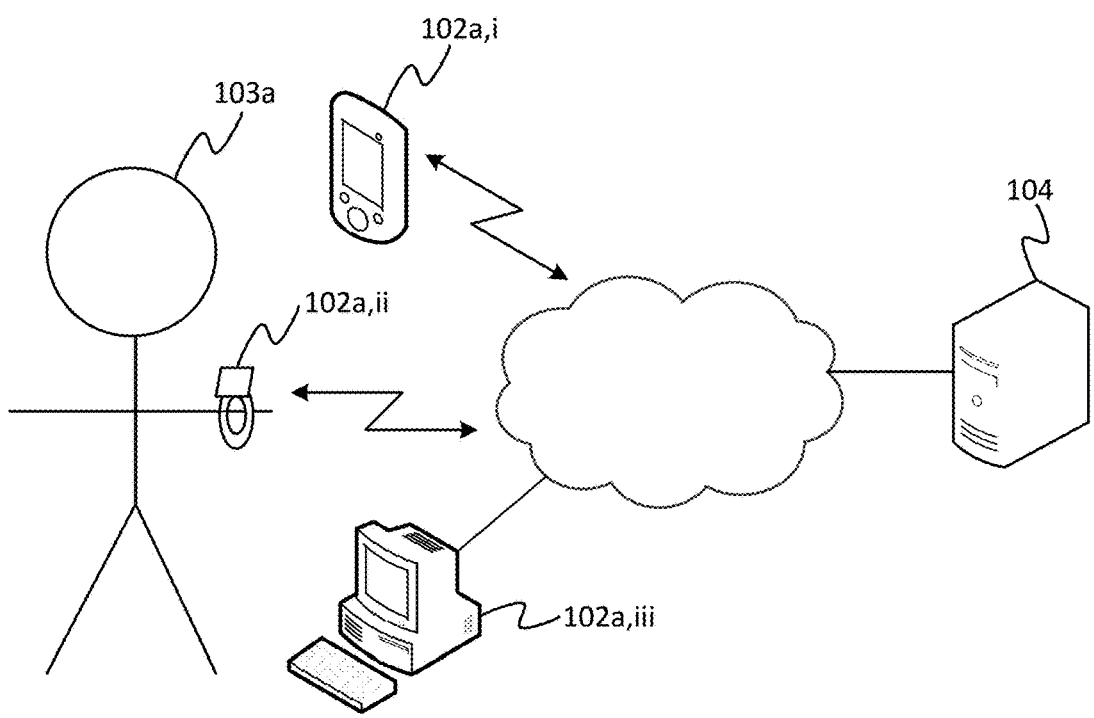

As mentioned, it would be desirable to increase the amount of information gained from the user. This may comprise, for example, increasing number of responses from a user in order to increase the available data quality, or increasing the amount of information content in the responses. It is recognised herein that the physical condition of the user when a question is asked may affect the likelihood of the user responding or the amount of useful information in their response. E.g. the physical condition could be a pattern of motion, or a facial expression as detected using facial recognition, etc. Accordingly, the presently disclosed system applies machine learning techniques to learn to output the questions at under circumstances that are more likely to result in the user responding to the question, or under circumstances that are most likely to elicit the most useful responses. This may be based, for example, on the user's historical usage, i.e. at what times and/or locations have they tended to respond in the past.

To achieve this, the present disclosure provides a system which trials the posing of questions to a user under circumstances of different metadata (e.g. time of day, location of the user device, means of question output, etc.). The system monitors the user's corresponding responses, and the metadata and the data on the user's response are fed to a machine learning algorithm as training data. The algorithm trains a model to optimize a reward function, wherein the reward function selects an optimum circumstance when the user is experiencing or exhibiting a particular physical condition to output the next question(s). The reward function may reward or promote an increase in the number of responses obtained from the user. For example, the training may be to maximize the number of responses per unit time, or to optimize a metric that is based on both the number of responses per unit time and the prediction quality. Alternatively, it may reward or promote the asking of subsequent questions at times or locations that are most likely to reveal the most amount of new information. In embodiments, the learning may also take into account circumstances such as how the question was output to the user (e.g. via chat bot or voice user interface, etc.) or the user's facial expression or vocal cadence when responding (detecting using image recognition or voice recognition respectively).

Thus for example, the system may be used to determine how the presentation (modality and/or content) of automatically generated user-facing prompts to complete a questionnaire impact users' readiness to respond; or how approaches to human-machine teaching and collaboration can be utilized to better determine when might be a good time, location or situation, to automatically prompt users to complete a questionnaire or part thereof. Embodiments may also combine such techniques with an emotional user interface, making use of data such as facial expression and voice cadence or intonation calibrated with interactive questioning as well as survey metadata.

In embodiments, deployment may be through the cloud and any one or more of a variety of potential user interfaces to the cloud service, such as multi-platform mobile apps, web forms, and/or chat-bots. For longitudinal monitoring questionnaires, the cloud service may learn the routes, times and/or other contexts (e.g. from mobile app position and/or motion data) in which the respondent is most likely to engage. In some embodiments the cloud service may also provide additional indirect emotional information from speech cadence and intonation.

FIG. 1 illustrates an example communication system 100 implemented over a network 101 in accordance with embodiments disclosed herein. The communication system 100 comprises a plurality of user devices 102 each associated with at least one respective user 103. Each of the user devices 102 may take any suitable form such as a desktop computer, laptop computer, tablet, smartphone, wearable smart device (e.g. smart watch or smart glasses), smart speaker, smart TV, or a dedicated health monitoring device (e.g. smart pill box, wearable health monitor, etc.). Also the different user devices 102 of the different users 103 need not necessarily all take the same form. Three users 103a-c and respective user devices 102a-c are shown for illustrative purposes, but it will be appreciated that there may be any number of users 103 and respective user devices 102 using the system at any given time.

The communication system 100 also comprises a server 104. A server herein refers to a logical entity which may comprises one or more physical server units located at one or more geographic sites. Where required, distributed or "cloud" computing techniques are in themselves known in the art. Each of the user terminals 102 and the server 104 is connected to a packet-switched network 101, which may comprise for example a wide-area internetwork such as the Internet, a mobile cellular network such as a 3GPP network, a wired local area network (LAN) such as an Ethernet network, or a wireless LAN such as a Wi-Fi, Thread or 6LoWPAN network. In embodiments the network 101 may comprise a plurality of such networks, e.g. the Internet plus one or more LANs and/or cellular networks via which one or more of the user terminals 102 connect to the Internet. Each of the user terminals 102 and the servers 104 may connect to the network 101 via any suitable network interface (not shown) incorporated in the respective terminal or unit, e.g. a wired modem connecting via a PSTN connection or an Ethernet connection, or a wireless modem connecting via a wireless connection such as a Wi-Fi, Thread or 6LoWPAN connection.

The server 104 is arranged to host a service provided to the users 103, via the network 101, accessed through via their respective user devices 102. The service comprises a monitoring service for monitoring a condition of the users 103, such as a health condition, by sending questions via the network 101 to be output to the users 103 through their user devices 102, and receiving back via the network 101 responses from the users 103 entered through their user devices 102. For any given user 103, any one, more or all of the user devices 102 used to provide the responses could be the same or different to those used to output the questions. The questions sent to each user may comprise different questions for the different users 103, or the same questions, or some the same and some different. Each of the user terminals 102 is installed with a respective instance of a communication client application for accessing the service via the network 101, each client instance being arranged to run on its respective user device 102. The client application may be a dedicated client application dedicated to the service in question, or may be a general purpose client application such as a web browser. The different user devices 102 may also use a mix of dedicated and general-purpose applications.

As shown in the lower half of FIG. 1, in embodiments any given one of the users 103a may have multiple user devices 102a, i-iii, each arranged to access the monitoring service provided by the server 104 in the manner described above. Three user devices 102a, i-iii are shown here for illustrative purposes, but it will be appreciated that in generally any number may be employed for a given user 103a. Further, though illustrated for a particular one of the users 103a, more generally any of the users 103a, 103b, 103c, etc., may have any number of user devices 102 for accessing the service.

Figure 2:
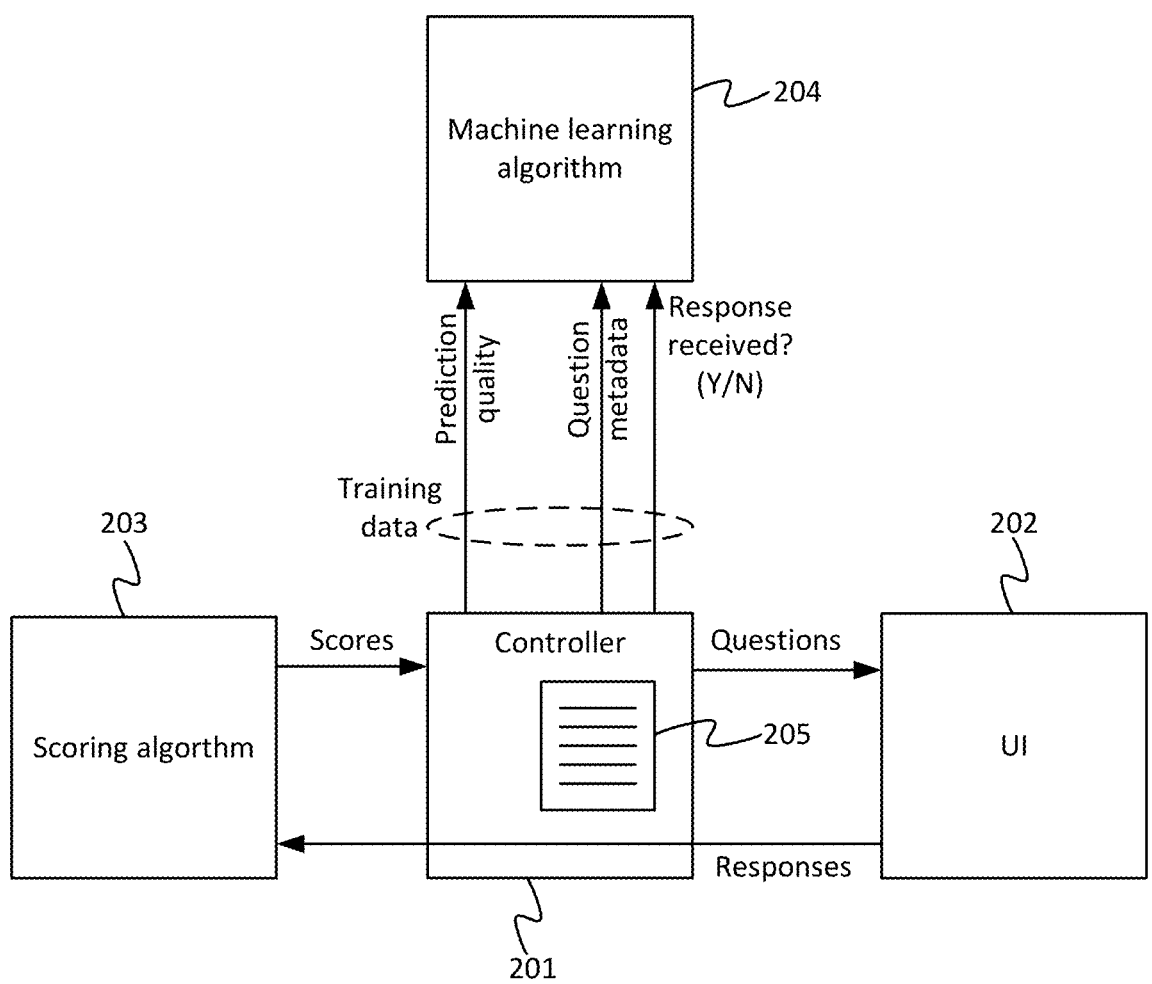
FIG. 2 is a schematic block diagram showing further example detail of the system.

FIG. 2 illustrates example components 201-204 of the communication system 100 for implementing the monitoring service. These components comprise a controller 201, a user interface 202, an optional scoring algorithm 203, and a machine learning algorithm 204. The controller 201 is operatively coupled to each of the user interface 202, the scoring algorithm 203 and the machine learning algorithm 204.

Each of the controller 201, user interface 202, scoring algorithm 203 and machine learning algorithm 204 may be implemented in the form of software code embodied on computer readable storage and run on processing apparatus comprising one or more processors such as CPUs, work accelerator co-processors or application specific processors implemented on one or more computer terminals or units at one or more geographic sites. The storage on which the code is stored may comprise one or more memory devices employing one or more memory media (e.g. electronic or magnetic media), again implemented on one or more computer terminals or units at one or more geographic sites. In embodiments, one, some or all of said components 201, 202, 203, 204 may be implemented on the server 104. Alternatively, a respective instance of one, some or all of these components 201, 202, 203, 204 may be implemented in part or even wholly on each of one, some or all of the user terminals 102, e.g. either as part of the respective client instance or in a separate application interfacing to the client instance via a suitable API (application programming interface). In further examples, the functionality of the above-mentioned components 201, 202, 203, 204 may be split between any combination of the user terminals 102 and the server 104. Again it is noted that, where required, distributed computing techniques are in themselves known in the art.

The controller 201 comprises a control function for coordinating the functionality of the user interface 202, scoring algorithm 203 and machine learning algorithm 204. It is preferably implemented on the server 104, but alternatively it is not excluded that it could be implemented in part or in whole on one or more of the user devices 102.

The user interface 202 refers to the functionality for interfacing with the users 103. The user interface 202 may comprise one or more constituent types of user interface, such as voice interface, a chat-bot, and/or a graphical user interface. The user interface 202 is presented to the users 103 through one or more I/O modules on their respective user device(s), e.g. speaker and microphone, touch screen, etc., depending on the type of user interface. The logic of the user interface 202 may be implemented on the server 104 and output to the user 103 through the I/O module(s) on his/her user device(s) 102. Alternatively some or all of the logic of the user interface 202 may also be implemented on the user device(s) 102 its/themselves.

The user interface 202 provides the means by which the questions are output to each user 103, and the means by which the responses to the questions are input by the user 103. For instance, the user interface 202 may comprise a voice interface whereby the questions are output audibly to the user 103 through a speaker on one or more of his/her user devices 102, and the responses are received through a microphone on one or more of his/her user devices 102 (which would be the same or different to that used to output the questions). In this case the user interface 202 comprises a voice recognition algorithm for recognizing the user's spoken responses (or other vocal responses).

As an alternative or additional example, in embodiments the user interface 202 may comprise a chat bot. For instance the questions may be output to the user 103 in the form of text on a visual display on one or more of his her user devices 102, and the responses are received back by the user typing the responses into a text field of the user interface presented on a visual display of one or more of the user's user devices 102, using a keyboard or keypad on one or more of his/her user devices 102. The chat bot may thus simulate the effect of communicating with another person via a text-based messaging system. The user device 102 on which each of the output display, input field, and keypad/board are implemented may be the same or different. In variants, the chat bot could take the form of an audio chat bot that outputs the questions audibly and receives the responses by voice recognition (see above) in a manner that simulates talking to a person. In yet further variants the chat bot may also comprise a video or animation of a person or character with whom the user 103 interacts.

In yet another alternative or additional example, the user interface 202 may comprise a graphical user interface (GUI) such as a point-and-click user interface or a touch screen user interface, e.g. through which the user 103 can select from amongst predetermined options for each response. In this case the questions may be output to the user 103 through a visual display of one or more of the user's user devices 102, and the user 103 may select the responses using a touch screen or screen plus pointing device (e.g. mouse or trackpad) on one or more of the user's user devices 102. Again, the device used for the question output may be the same or different to that used to input the responses. In embodiments, any one or more of these or other types of user interface, in any combination on any one or more user devices 102, may be used to output the questions to the user 103 and receive the responses back from the user 103.

The scoring algorithm 203 is configured to generate an overall score from the responses to predict a condition of the user 103 form his/her responses, in embodiments to predict the onset of certain condition of the user 103, e.g. a health condition such as asthma, depression, or heart disease, etc. In embodiments the scoring algorithm may take the form of a pre-trained neural network or other statistical learning method, or alternatively a predetermined set of rules. The scoring algorithm 203 is preferably implemented on the server 104, but alternatively it is not excluded that it could be implemented in part or in whole on one or more of the user devices 102.

The machine learning algorithm 204 may comprise another neural network, plus an algorithm such as a back-propagation algorithm for training that neural network. Alternatively other forms of machine learning algorithm such as a clustering algorithm are not excluded. The machine learning algorithm 204 is configured to take as training data: i) data on the responses from each given one of one or more of the users 103, and ii) for each question asked, a value of one or more pieces of metadata associated with the question.

The data (i) on the user's response includes at least, for each question posed, an indication whether or not the user responded at all. In embodiment the data on the user's response may also include further data qualifying a manner of the response, such as information on a facial expression or vocal intonation of the user 103 when responding.

The associated metadata (ii) describes one or more of: the nature of the question (e.g. a format of the question), the way it was output (e.g. audibly or visually), and/or contextual circumstances under which it was output (e.g. the user's location when asking the question). The one or more pieces of metadata associated with the question comprise at least a time and/or a location at which a question was output to the user via the one or more user devices. The machine learning algorithm 204 is configured, based on such training data, to train a model (e.g. neural network) to optimize a reward function (or performance measure) which places a positive training reward on, for example, increasing the number of responses from the user 103 per unit time (i.e. response rate, though note this term as used herein does not necessarily imply a periodicity in the responses). Thus the machine learning algorithm 204 learns which values of the metadata (at least a time and/or location) that tend to increase the number of responses from the user 103. This will be discussed in more detail shortly. Instead of increasing the number of responses from the user 103, the machine learning algorithm 204 may learn values of the metadata that are more likely to result in a response from the user 103, more likely to result in a greater level of engagement from the user 103, and/or more likely to increase the amount of information gained from the user 103 per question.

The machine learning algorithm 204 is preferably implemented on the server 104, but alternatively it is not excluded that it could be implemented in part or in whole on one or more of the user devices 102. In the case of multiple users 103, a separate model may be trained specific to each user 103, or alternatively a common model may be trained for a group of some or all of the users 103. In the case of a common model, an advantage of a server-based implementation for the machine learning algorithm 204 is to exploit the central processing resources of the server 104 to train the model for the group.

The functionality of the controller 201 (the control function of the code) is now discussed in more detail. Embodiments may be described from the perspective of a given user 103a, but in the case of a multi-user system, it will be appreciated that similar techniques may be put in place for each user 103, either individually for each user 103 to learn a respective model for each user 103, or pooling the data on a group of users 103 to train a common model for the group.

The controller 210 is configured to control the user interface 202 to output questions to the user 103a via one or more of his/her user devices 102a, i-iii; and to receive back responses to some of the questions from the user via one or more of the user's user devices 102a, i-iii. Again, the device(s) 102 used to output the question could be the same or different to the device(s) 102 used to receive the response. The user interface 202 may be implemented by the server 104 but is manifested through a suitable I/O module or modules of the relevant user devices 102, e.g. speaker, microphone, touchscreen, etc. The server 104 comprises a network interface which it uses to control the user device(s) 102, via the network 101, to make the relevant elements of the UI 202 available to the user 103a.

The questions are selected from amongst a pool of questions stored in a question database 205, which may be considered part of the controller 201. The output questions may comprise repeated instances of the same question (asking the same thing, i.e. the same question content), and/or different questions (asking different things, i.e. different question content). The questions relate to a condition of the user 103a in order to monitor that condition. In embodiments the condition in question is a health condition such as asthma, depression, fitness, etc. The monitoring could be for the purpose of making a prediction on a future state of the user's condition, e.g. to predict the onset of a problem with the user's health; or just for the purpose of information for the user, a health practitioner or a clinical trial, etc. The questions may be output to the user 103a at different times and/or locations throughout the day, week or month; e.g. by individual ones or subsets of the questions of a questionnaire at different times throughout the day or week instead of all at once at the same time of day or week.

As mentioned, the user interface 202 through which the questions are output to the user 103a may comprise a voice interface, chat bot, or graphical user interface. For instance the user 103a could have an audio device or general purpose smart device carried or worn about his/her person, or placed by his/her pill box. Such a device may then be used to surface an audio chat bot that talks to the user 103a to ask questions and receive back the user's corresponding responses. As another example, the user 103a could have a portable or wearable device with a display, such as a smart watch, smartphone or tablet, through which a video or animated chat bot is provided.

In further alternative or additional embodiments, one or more of the user devices 102a, i-iii may comprise a sensor device, e.g. a wearable or portable sensor device worn or carried about the user's person. For instance, such a device could take the form of an inhaler or spirometer with embedded communication interface for connecting to the controller 102, preferably a wireless interface for connecting via a wireless medium such as Wi-Fi, Bluetooth, 6LoPAN, etc. In such cases, one or more of the questions may ask the user 103a to respond by submitting a sensor reading from the sensor device.

As one example application, patients are supposed to monitor asthma control by keeping a peak flow diary. This is a twice-daily log of peak flow measurements and a symptom log based on the Asthma Control Test (ACT). The ACT questions are broadly: a) have you used your reliever inhaler today; b) have you had any symptoms (e.g. shortness of breath, chest tightness, wheeze or coughing); c) have you woken at night with asthma symptoms; and d) do you feel that you can't keep up with your normal activities. Many patients do not engage with this as it is time-consuming and off-putting.

In embodiments disclosed herein, the questions in the question database 205 may comprise any or all of the above questions, and optionally also a question asking the user 103a to submit an inhaler or spirometer reading. These questions may be output to the user 103a individually in gradual succession over the course of the day and/or week, preferably via an intuitive and accessible user interface 202 such as a voice interface or chat bot, and preferably via a convenient device such as a wearable or portable smart device, or an everyday device around the home or office.

Note: the techniques disclosed herein could also apply to other applications, not just monitoring a health condition of the user 103a. For instance another example application would be market research. Here the monitored condition may be a measure of a disposition of the user 103a toward purchasing a certain product (goods or services). Another example would be to monitor a user's political stance. Such matters can constitute an objectively measurable condition (e.g. in terms of a predicted probability such as the likelihood of purchasing a product or voting a particular way). Embodiments herein may be illustrated in terms of monitoring a health condition, but it will be appreciated that this is not limiting and any of the described techniques can also be applied to other applications).

Whatever the application, the controller 201 is configured so as, over time, to control the outputting of the questions so as to try the outputting under circumstances of different values for each of one or more items of metadata, i.e. parameters of the question, the way in which it is asked or the context in which it is asked.

This does not necessarily mean the controller 201 can control the metadata per se. Rather, some types of metadata may simply passively reflect the context in which the question is asked. Such metadata may be referred to herein as contextual metadata, i.e. one or more pieces of contextual information reflecting a context in which the questions are asked. Contextual metadata is metadata that the controller 201 cannot control. Examples of such metadata may include any one or more of: I) a location of the user 103a when the questions are asked, II) a pattern of motion of the user 103a when the questions are asked, III) an activity being conducted by the user 103a when the questions are asked, and/or IV) one or more indicators of a mood of the user when the questions are asked.

These are not features of the system that can be controlled per se. However, the controller 201 can time the output of the questions to coincide with a certain value of the contextual metadata. E.g. the controller 201 can wait until the user 103a is detected to be at a certain location and wait until then to pose question. Or alternatively, the controller 201 can simply output questions randomly or with no particular correlation to the contextual metadata, so that over time the questions will tend to be output with different values of the metadata.

In the example of the user's location, this can be monitored by a portable or wearable device disposed about the user's person (plus any one or more of a variety of known localization technologies such as triangulation, trilateration, multilatertion or fingerprinting relative to a network of known nodes such as WLAN access points, cellular base station, satellites, or anchor nodes of a dedicated positioning network such as an indoor location network). The location of the user 103a may be relevant metadata for learning when to output questions, since there may be certain locations (e.g. at work or out shopping) where it may be less convenient for the user 103a to answer questions than when at other locations (e.g. at home). Further, the location technology, and/or one or more motion sensors such as accelerometer, gyroscope and/or magnetometer, may be used to track the motion of the user 103a. This could be relevant since, for example, it may be less convenient to respond to questions when the user 103a is moving more, e.g. when out running. Metadata on the activity of the user 103a may also be gathered in other ways, e.g. by one or more cameras in the user's environment plus an image recognition algorithm, or by referencing an electronic schedule of the user 103a (e.g. the calendar in his/her email client).

The indicator(s) of mood may comprise one or more of: a facial expression of the user when the questions are asked, a change in heart rate when the questions are asked, a change in cadence of speech when responding through a voice interface, a change in intonation when responding through a voice interface, a change in cadence of typing when responding in a chat-bot user interface, and/or a change in sentiment when responding in a chat-bot user interface. These may be relevant since they reflect the user's disposition toward responding to questions. The metadata on the user's facial expression may be collected for example from a front-facing camera of the user's device 102 (e.g. smartphone or tablet), and/or from one or more other camera devices arranged in the user's environment. The facial expression metadata used for the training in the present method may comprise the raw image data, or alternatively the image data may be pre-processed by a facial recognition algorithm to extract one or more expression features for use as the metadata. The metadata on the user's voice intonation or cadence may be collected from a microphone in the user's device 102. The metadata used for the training in the present method may comprise the raw sound samples or one or more features extracted therefrom by a voice or audio processing algorithm. The metadata on the user's heartrate may be collected from a wearable heartrate monitor device worn about the user's person.

The metadata may alternatively or additionally comprise one or more controllable parameters of the questions or a manner in which the questions are output, i.e. parameters that the controller 201 is able to control. For example the one or more controllable parameters may comprise one of more of: A) a frequency at which the questions are asked, B) which questions are asked from amongst a predetermined set, C) an order in which the questions are asked, D) how many questions are asked per sitting, E) a format in which the questions are asked, F) a time of day and/or week at which the questions are asked, G) which user device 102a, i-iii is used to ask the questions, and/or H) whether the questions are output audibly or visually. For instance, the frequency of posing questions to the user 103a will likely be relevant: increasing the frequency of asking questions increases the opportunities for response, but beyond a certain point the frequency of interaction may start to annoy the user 103a and thus have a counter-productive effect in that the user 103a may stop responding. Further, the means of interaction (e.g. smartphone, tablet or smartwatch, etc.; or voice interface vs. text-based chat-bot) may also affect the user's tendency to respond. Some users may also respond more or less depending on the form of the question (e.g. a degree of personal familiarity or colloquialism used to address the user 103a, such as whether addressed by first name or surname).

The response for each question is thus associated with a value for each of a set of one or more pieces of metadata, which may comprise contextual information and/or controllable parameters.

Other contextual information such as sleep quality inferred from personal device data may be used not only to personalise user-prompting patterns but also to add to the predictive information of user-responses in such contexts. For example the use of a wearable sleep monitor might reveal a serious of short night sleeps of only 5 hours, when the person's typical sleep pattern is 8 hours. This data deviation could be used as a prompt to initiate a sleep quality questionnaire or keep administering sleep questionnaires until the person has achieved their 8 hour routine again.

For each question output to the user 103a, the controller 210 is configured to monitor whether or not the user 103a responds when the questions are output with the different metadata values. The controller 201 supplies the metadata values, and a corresponding indication of whether the user 103*a* responded, as training inputs to the machine learning algorithm 203. Based on this data, the machine learning algorithm 203 is trained to learn a value of each of the one or more items of metadata which optimizes a predetermined reward function, and based thereon select a time and/or location at which to output one or more subsequent questions. For example, the time and/or location selected is the time and/or location that maximises the reward function.

The reward function may optimise a number of said responses per unit time, so as to create at least a positive bias in the training toward increasing the number of responses per unit time. For example, this reward function may comprise an indication of the number of responses per unit time, such that said optimizing comprises maximizing the number of responses per unit time. Alternatively the reward function could be a combined metric based on the number of responses per unit time and one or more other factors, such as prediction quality (discussed in more detail shortly).

The machine learning algorithm 203 may for example take the form of a first neural network and feedback algorithm arranged to train the neural network. A machine learning algorithm comprises a model (e.g. neural net) which maps an input or input vector (set of inputs) to an output or output vector (set of outputs). It also comprises a training algorithm (e.g. a feedback algorithm such as a back-propagation algorithm in the case of a neural net). The training algorithm trains the mapping of the model (at least in a supervised approach) based on training data comprising i) multiple example values of the input vector, and ii) the corresponding experienced values of the output(s) that resulted from those training inputs. Based on this data, the training algorithm can adapt the mapping of the input(s) to the output(s) in its model so that the mapped outputs of the model will tend towards matching the experienced outputs in the training data. This model can then be used to subsequently infer a value of the output(s) for any given value of the input(s).

Figure 3:
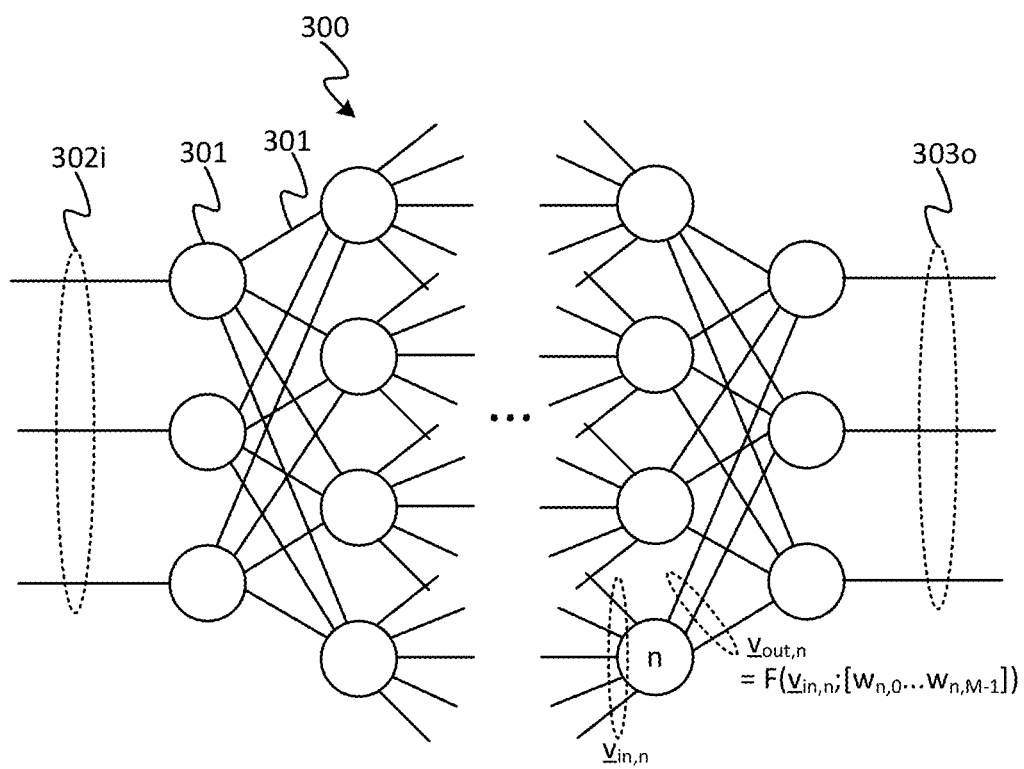
FIG. 3 is a schematic illustration of a neural network.

As shown in FIG. 3, in embodiments the model comprises a neural network 300. A neural network comprises a graph of interconnected nodes 301 and vertices 302 between nodes, all implemented in software. Each node 301 has one or more input vertices and one or more output vertices, with at least some of the nodes 301 having multiple input vertices per node, and at least some of the nodes 301 having multiple output vertices per node. The input vertices of one or more of the nodes 301 form the input to the graph 302*i* (the input vector in the case of multiple input vertices), and the output vertices of one or more of the nodes 301 form the output of the graph 302*o* (output vector in the case of multiple output vertices). Further, the output vertices of at least some of the nodes 301 are connected to the input vertices of at least some others of the nodes 301. The vertices 302 forming the connections to and from nodes 301 are sometimes also referred to as edges.

Each node 301 represents a function F of its input vertices, the outputs of the function being the output vertices of the node, such that the values of the output vertices of the node 301 depend on the values at its input vertices according to the respective function. The function of each node 302 is also parametrized by one or more respective parameters w, sometimes also referred to as weights (not necessarily weights in the sense of multiplicative weights, though that is one possibility). Thus the relation between the values of the input and output vertices 302 of each node 301 depends on the respective function of the node and its respective parameters.

Before being used in an actual application the neural network 300 is first trained for that application. Training comprises inputting training data to the inputs 302*i* of the graph and then tuning the weights of the nodes 301 based on feedback from the output(s) 302*o* of the graph. The training data comprises multiple different input data points, each comprising a value or vector of values corresponding to the input vertex or vertices 302*i* of the graph 300. With each training data point, the resulting output value(s) at the output vertex or vertices 302*o* of the graph are observed, and this feedback is used to gradually tune the weights of the nodes 301 so that, over many pieces of experience data, the weights tend towards values which make the output(s) of the graph 300 as close as possible to the actual observed value(s) in the training data across the training inputs (for some measure of overall error). I.e. with each piece of input training data, the predetermined training output is compared with the actual observed output of the graph 302*o*. This comparison provides the feedback which, over many pieces of training data, is used to gradually tune the weights of the various nodes 301 in the graph toward a state whereby the actual output of the graph will closely match the desired or expected output for a given input vector. Examples of such feedback techniques include for instance stochastic back-propagation.

Once trained, the graph 300 can then be used to infer a value of the output or output vector 302*o* for a given value of the input or input vector 302*i*, or vice versa.

Machine learning algorithms such as those based on neural networks are, in themselves, known in the art. The present disclosure employs machine learning for a new application, i.e. to select an optimal time and/or location at which to output a subsequent question. The machine algorithm may learn which times and/or locations increase the response rate of a user 103*a*, and/or which increase the amount of information gained from the next question output to the user 103*a*.

In the present case, each input data point in the training data corresponds to the outputting of one of the questions to the user 103*a* (e.g. in any of the ways discussed earlier). Each input data point comprises the values of the one or more items of metadata associated with the outputting of the respective question, e.g. time of day, means of output (e.g. audio vs. text, wearable vs. handheld device, etc.), and/or the format of output (e.g. degree of formality), etc. This could comprise any of the types of metadata discussed earlier. The one or more input(s) 302*i* to the graph or model 300 correspond to the one or more items of metadata.

The training data further comprises, for each input data point, a corresponding indication of whether or not the user 103*a* replied when the question was posed under the circumstances of the respective values of the metadata—i.e. a corresponding output for each input data point in the training data. The output 303*o* of the graph 300 may represent a probability that the user 103*a* responds.

Based on this training data, the machine learning algorithm 203 trains its model (e.g. trains the weights w in the neural net 300) to produce a mapping between the input(s) and output(s) of the model (e.g. between the input vertex or vector 302*i* and output vertex or vector 302*o* in the neural net 300) which will infer the likelihood of eliciting a response from the user 103*a* for a given input value of the metadata or metadata vector.

The trained model can then be used to infer the value(s) of the one or more items of metadata which will tend to result in an optimal value of a reward function (or performance measure). The reward function may comprise at least the number of responses per unit time from the user (in a manner that places a positive reward on increasing the number of responses per unit time). E.g. the reward function may be the number of responses per unit time, such that said optimizing comprises maximizing the number of responses per unit time. Alternatively the reward function may be a metric striking a balance between the number of responses per unit time and one or more other factors such as prediction quality (the quality of the prediction of the user's condition, e.g. health condition). Note that number of responses per unit time may be expressed as a probability of response. Note also that terms such as "optimize" or "maximize" herein do not demand 100% perfection, but rather are to be judged within the bounds of what is practically achievable given the training data.

Based on the training, the controller 201 continues outputting further ones of the questions to the user 103a, each at a respective time and/or location based on the learned values of the metadata in order to optimize a reward function. For example, the reward function may measure the likelihood of a user responding to a question. The reward function may measure the amount of information gained from a response to a question. The reward function may measure the uncertainty in a predicted answer. Optimizing the reward function may increase the number of responses from the user per unit time. In the case of contextual metadata such as user's location, state of motion, mood, etc., this may comprise waiting until the corresponding contextual circumstances are detected before outputting the next question; e.g. waiting until the user gets home, stops running, or is in a good mood according to his/her facial expression. In the case of controllable metadata, e.g. time of day, means or mode of output, form of question, etc., the controller 201 can actively control the relevant parameter(s) in order to output the question in the optimal fashion.

Thus by asking a number of questions over time and/or at different locations and varying the question, the way in which it is asked and/or the context in which it is asked, the system can learn how to interact with the user 103a in order to maximize or at least increase the responsivity of the user 103a. A traditional questionnaire can be the starting point for outputting the questions at the start of the process, but then as time goes on, the system will learn through frequent use and interaction how to present the questions so as to maximize the accuracy of the responses, the efficiency of the questionnaire (in terms of gaining more information in fewer questions), and/or the response rate, and will get better the more it interacts with the user 103a.

For instance, the metadata may comprise how often the system interacts with the user 103a (e.g. per day or per week). Up to a point, asking questions more often will increase the amount of information gained and the number of responses. However, if the system attempts this too often, the user may start to ignore the questions or their responses may begin to lack detail and therefore this has a self-defeating effect. Hence it would be desirable to learn the optimal time and location at which to output questions to the user 103a. Additionally, it would be desirable to learn the optimal frequency with which to output questions to the user 103a, e.g. the optimal number of times per day and/or week.

Another alternative or additional piece of metadata taken into account may be the time of day at which the questions are asked, as some users may be more or less responsive at certain times of day. By trying asking questions at different times of day the system can learn when best to interact with the user 103a to elicit a response.

As another alternative or example, the type of device 102 and/or UI modality used to output the questions may make a difference: the user 103a may be more likely to respond though some devices 12 than others, or certain UI types than others.

Another example factor may be the form of the question, e.g. how formally it is presented, such as whether it addresses the user 103a by his/her first name (given name) or surname (family name), or employs specific linguistic strategies (e.g. 'positive politeness') to invite a response. The system could try addressing the user more or less formally, more or less politely, and learn which way is most likely to induce the user 103a to respond.

In further alternative or additional examples, sensor data from e.g. a camera, localization system, motion sensor(s) and/or heartrate monitor may be used as metadata. For instance a camera may be arranged to capture an image of the user's facial expression, which may be indicative of a mood of the user, or the heartrate sensed using a heartrate monitor worn by the user's may also be indicative of the user's mood. The user may be less likely to respond when in a bad mood (e.g. grumpy or stressed), so it would be useful if the system learned this and avoided outputting questions at such times. The user's location and/or state of motion may also be relevant—e.g. when the user 103a is out shopping or running, this may not be a good time to ask questions.

In one particular example embodiment, the system seeks to improve the predictive value of questionnaire responses with facial expression information taken from the forward-facing camera of devices presenting questions to the user. The system learns the combined score of a long questionnaire such as SF36 (quality of life by 36 questions) from a random subset of k questions plus facial expression information repeated within individual participants daily over say 1 month. The subset size k that maximises response rate might be the subject of a nested experiment, mindful that feedback to the user of a meaningful score may be traded off against the convenience of a brief interaction.

Various types of relevant metadata have already been discussed previously, and any one or more of these, and/or other types, may be taken into account to learn when best to interact with the user to elicit a response.

In embodiments, the controller 201 is configured to supply the responses to a scoring algorithm 204 to generate scores predicting the condition of the user 103a (e.g. health condition) based on the responses. E.g. the score may take the form of a number on a scale such as one to five representing the predicted current severity of the user's health problem (e.g. asthma) or the likelihood of a problematic event (e.g. asthma attack). The scoring algorithm 204 may for example comprise a second, pre-trained neural network (different from the first neural network being trained to increase the response rate), wherein this second neural net has been pre-trained to predict the likelihood of a state of the user's condition, e.g. an onset of the health problem, based on responses to the questions. Alternatively the scoring algorithm may comprise a set of predefined rules, e.g. composed by a panel of human experts.

In embodiments, the reward function which determines the optimal metadata value(s) is not (or not just) the number of responses per unit time. Rather, the reward function may (also) comprise a measure of prediction quality based on the scores generated by the scoring algorithm 204, thus creating a positive bias in the training both toward increasing the prediction quality and increasing the number of responses per unit time. E.g. the reward function may comprise a combined metric combining both the number of responses per unit time and the prediction quality. In such embodiments, the controller 201 uses the machine learning algorithm 203 to find a value or values of the one or more items of metadata that, accordance to the inference of the machine learning algorithm, will produce an optimal value of the combined performance metric.

The idea here is that, although obtaining more responses provides more data for making a prediction, after a point this may start to have a negative effect on the quality of the data. For example, if the user is induced to respond too often, then he/she might stop thinking carefully enough about the answers (starting to answer on "auto pilot"). Therefore when an increasing number of responses starts to impede quality, it may be desirable to reign back the response rate. By training to optimize a combined reward function (e.g. combined metric) taking into account both response rate and prediction quality, then embodiments of the presently disclosed system and method advantageously strike a balance between quality and the number of response per unit time.

As a simple example, the reward function may comprise a weighted sum of number of responses per unit time and prediction quality, and the optimization may seek to find values of the metadata which maximize this sum. At some point where the number of responses starts to have too much of a detrimental impact on the score quality, then the metric will start to decrease with increasing number of responses. The exact form of the metric may be a design choice, as long as it rewards both increased response rate and greater prediction quality (the exact form of the metric affects the relative significance placed on each, which may be a design choice, e.g. based on experimentation and/or application aims). Also note of course that minimizing a metric that places a numerically negative value on the two factors is equivalent to maximizing a metric that places a numerically positive value on them.

The estimate of the prediction quality, for a single user or a group of users, may for example comprise: the measured uncertainty of the overall score based on the statistical patterns of its component data (responses to questionnaire elements), the variability in change over time of the overall score, subsequently obtained empirical information on the condition of the user, or a combined metric based on any of these and/or other measures. The statistical variation may for example be measured in terms of the coefficient of variation in the overall scores obtained for the user 103a in question over time. In the case of comparing with empirical results, these may be obtained from personal sensor word or used by the user 103a, and/or from a visit by the user 103a to a doctor or other health practitioner.

In further variants of the above, the controller 201 may be configured to configure to perform said training in a two-stage process over a first phase and a second phase. In this case, in the first phase (a "burn in" period) said performance measure is purely the number of responses per unit time. Thus in the first phase, the system purely optimizes for maximizing the number of responses per unit time, regardless of quality. In the second phase however (e.g. a predetermined amount of time after the first phase), the performance measure switches to comprising at least the measure of prediction quality based on the scores, thus at least create a positive bias in the training toward increasing the prediction quality. In this second phase, the performance measure may consist of only the measure or prediction quality, such that said optimization comprises maximizing the prediction quality according to said estimates. Alternatively in the second phase, the performance measure may comprise both the measure of prediction quality and the number of responses per unit time (so as to then strike a balance between the two potentially competing factors). Thus in a period when the system first starts running for a given user 103a (burn in period), the system just optimizes for response rate, but then later it also starts optimizing for quality.

The following now describes another embodiment in which the reward function promotes not the number of responses, but rather determines which next question to output to the user 103a, and in which circumstances to gain the most useful information content from the next question. Bayesian experimental design methods in machine learning can be utilized to adapt the choice of the questions presented to users in a personalized manner. The decision of the next question to ask may be conditioned on the previous answers from the user. For example, if the user hints that they have pain in the left knee, the next question would more likely to be whether the symptom is shown in the right knee to determine whether the pain is neuropathic or nociceptive effectively. Other questions such as whether the patient experiences seizures would not be as informative in this exemplary scenario.

The adaptive questionnaire using Bayesian experimental design is also part of the machine learning algorithm 204. Efficient dynamic discovery of high-value information (EDDI) is enabled through building an end-to-end system that utilizes amortized inference with partially observed data, and a principled information acquisition function inspired by Bayesian experiment design.

Figure 4:
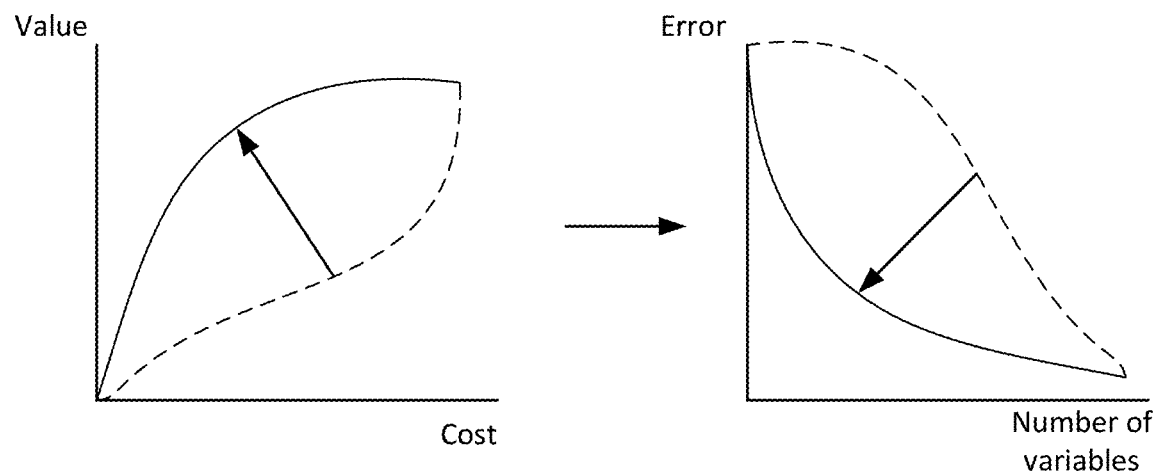
FIG. 4 is a schematic illustration of a goal of the adaptive questionnaire.

FIG. 4 illustrates an aim of EDDI. In general, it is preferable for the system to obtain the maximum value with the minimum cost. In this case, we would like to receive the maximum information about the user's health-status (value), which for example, can be in the form of a score, using the least number of questions (cost). Converting to the machine learning objective in this application scenario; we would like to use the minimum number of questions for each user to obtain the minimum error on the score.

Figure 5:
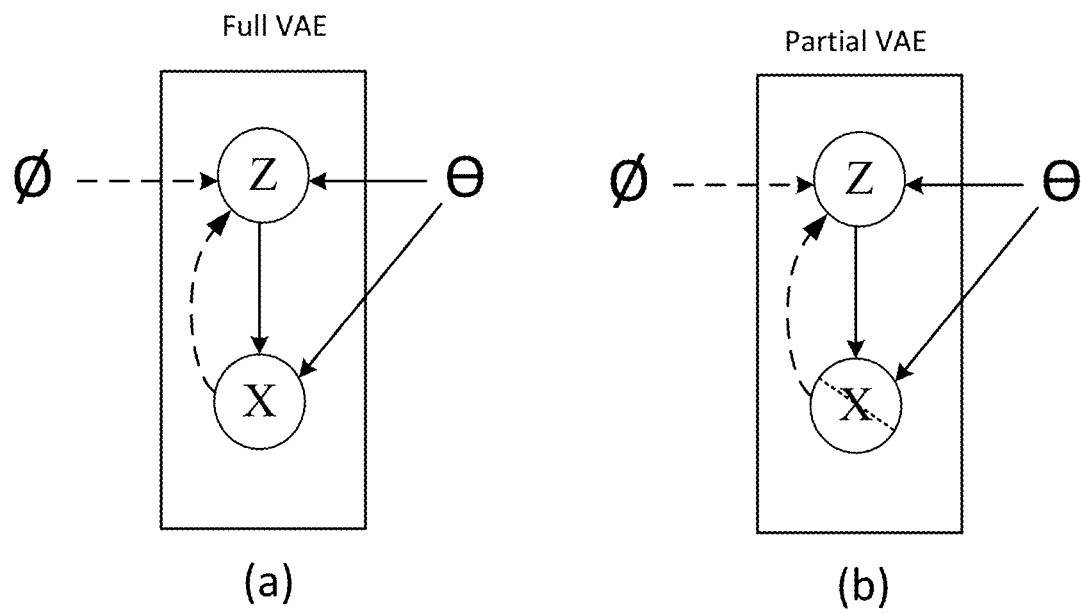
FIG. 5 is a schematic illustration of a variational autoencoder (VAE) with full observation and partial observation.

The EDDI system comprises two parts. The first part is a novel method, namely partial VAE (variational auto-encoder), for estimating an unknown variable using any number of answered questions. Here, each question is treated as an independent variable. The presentation of questions needs to be dynamic and personalized for each user conditional on the previous answers. The model can utilize a set of variables with arbitrary length. In general, we extend the VAE to a set setting, thus enabling it to use partial observations, as presented in FIG. 5. FIG. 5(a) shows the graphical representation of traditional VAE, where X (all answers for all questions in this case)—are fully observed (known). θ and φ are parameters for deep neural networks, which are served as function estimators to enable amortization. FIG. 5(b) shows the graphical representation of the Partial VAE, where a set structure for the neural network is used for the partially observed X, i.e., only some of the questions have been answered. To enable the set parameterization, a symmetric operator, such as summation, is chosen. In this way, the model can take any number of answered questions and predict the unobserved (unanswered) ones and the score in a probabilistic manner.

With partial VAE as the base, Bayesian experiment design can be utilized to present questions to the user adaptively. This is the second component of the EDDI system. As we may be interested in a statistic y, such as some scores, and we can obtain $p(y|x_p)$, the useful information estimated using partial VAE, where $x_p$ is any subset of answers. The reward function that we would like to maximize is presented as follows:

$$R_y(i,x_o)=E_{x_i \sim p(x_i|x_o)}[KL(p(y|x_i,x_o)\|p(y|x_o))]$$

where $x_o$ is the observed answers until now, and i indicates the next question that we would like to present to the user. In general, we select the next question to ask to maximize the information rewards. In this way, we can use fewer questions to maximize the information about the statics of interest, such as scores on health-status. We also propose a novel derivation to estimate the reward function efficiently.

In summary, EDDI contributes in the machine learning modular (204). It utilizes machine learning technology to dynamically present (new) questions to each user in a personalized manner.

Partial Variational Autoencoder (VAE)

A traditional VAE, referred to as a Full VAE hereinafter, has an inference model and a generative model. The aim of the Full VAE is to learn a mapping from observed variables $x_o$ to a latent space variable z, and to learn a mapping from z to estimate variables x. The inference model takes observed variables $x_o$ as inputs and outputs multiple distributions, each distribution representing a respective observed variable. The distributions are sampled to generate a vector $\bar{Z}$. The generative model takes vector $\bar{Z}$ as an input and outputs estimates of variables x. The Full VAE is trained on sets of variables that each have an observed value.

Figure 6:
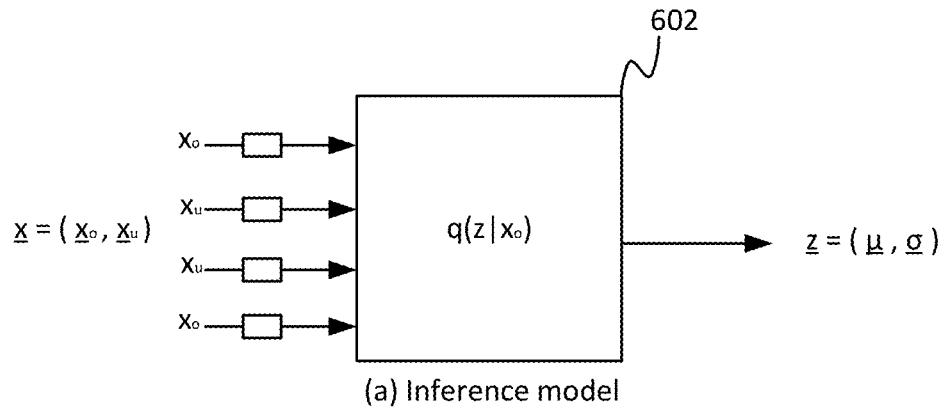
FIG. 6 is a schematic illustration of an example partial variational encoder.
Figure 6:
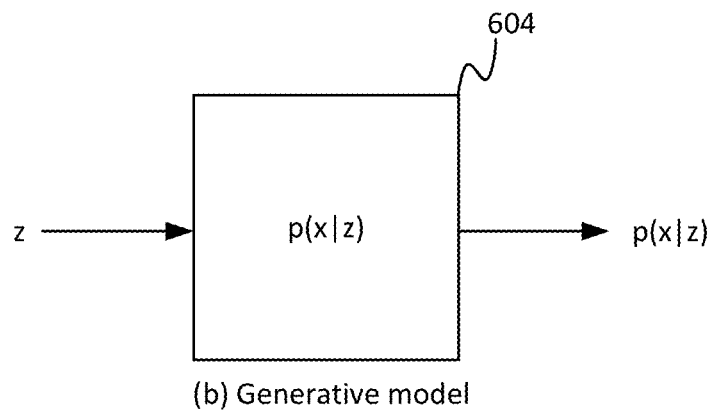

A partial VAE aims to learn a mapping from variables X to a hidden variable z. However, in contrast to a Full VAE, the inference model has to cope with receiving a vector $\bar{X}$ comprising an arbitrary set of input variables (or values) containing both observed variables $x_o$ and unobserved variables $x_u$. The partial VAE therefore needs to learn inferences based on an incomplete set of input values. Referring to FIG. 6, $q(z|x_o)$ defines the inference model 602 mapping observed input values $x_o$ to the hidden variable Z. By assuming $q(z|x_o)$ approximates to $p(x|z)$, a complete set of variables $\bar{X}$, including both observed variables $x_o$ and unobserved variables $x_u$ can be estimated (i.e. output by) generative model 604 given a sample of z.

Figure 7:
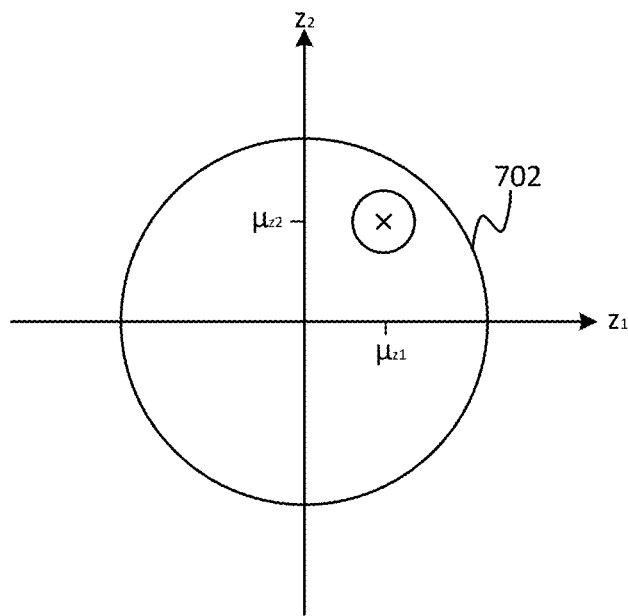
FIG. 7 is a schematic representation of an example hidden variable in latent space.

The inference model $q(z|x_o)$ is a function of which input values are present and their respective values. The inference model outputs values describing distributions of z in latent space, i.e. a range of possible values of z. The model may output one or more distributions of z, with each distribution described by a value representing a prediction of z and a value representing an associated error in that prediction. For example, the model may output sets of values (first values), each pair having a mean value of z, $\mu z$ and an error value, $\sigma z$ (e.g. a standard deviation or variance). The distributions may be normal distributions centred on the mean value of z. The latent space z can have any number of values $z_1$ to $z_N$. FIG. 7 illustrates an example of two mean values of z plotted in latent space 702.

Embodiments of the present invention employ machine learning techniques to learn a mapping between an arbitrary set of responses to questions output to a user and a health condition (the hidden variable). That is, the model $q(z|x_o)$ is a function of the questions output and the responses to those questions. Whilst the latent space z does not represent any definable quantity, it contains useful information for making predictions about real-world properties, e.g. about the health condition. For example, the grouping of data points in z space may represent similarities in the input data.

Note that z is never truly observed but values of z in latent space can be estimated from the inference model $q(z|x_o)$. Each distribution is (randomly) sampled to generate a vector $\bar{z}$ as an input to a generative model 604. The generative model $p(x|z)$ generates likely outcomes for the set of variables $\bar{X}$, including both the observed and unobserved variables. The generative model generates a probability distribution for each variable x. Each probability distribution may be represented by a set of (second) values. For example, the second values may comprise an estimate of the value (e.g. a mean) and a value representing an associated error in that estimate (e.g. a standard deviation).

In embodiments of the invention, the generative model 604 may output a probability of a response to each of the questions in the set of questions. For example, if the question is a Yes/No question, the generative model may predict that there is a 20% probability that the response is Yes and an 80% probability that the response is No. Therefore a response to an unanswered question may be predicted.

Figure 9:
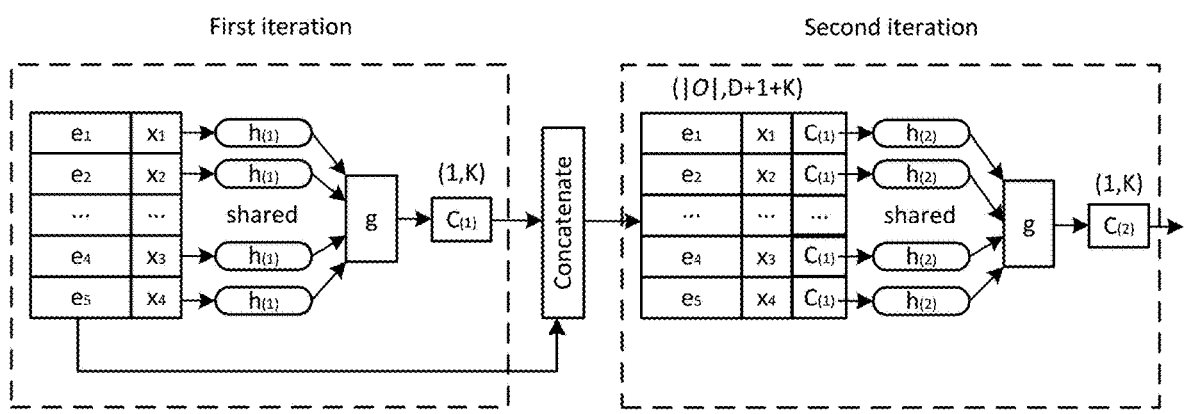
FIG. 9 is a schematic illustration of an example iterative point net for a partial VAE network, and FIGS. 10a to 10h schematically represent an example of how the information content gained per question and the estimate of variables change with each question asked.

Each model may be a machine learning model such as, for example, a neural network. That is, the inference model may be a first machine learning algorithm and the generative model may be a second machine learning algorithm. The first and second machine learning algorithms may employ different types of machine learning techniques. The partial VAE is trained with sets of training data in order to learn the mappings from $x_o$ to z and from z to x. The training sets contain sets of questions and their responses. Some sets may be complete, i.e. each question has a response, whilst some sets may be incomplete, i.e. some questions are unanswered. One or more sets may be incomplete. That is, a set of questions may be completely unanswered. The first dashed box in FIG. 9 illustrates how sets are handled in Partial VAE. The value and identity information of each input are mapped though a small neural network h first. Then a symmetric operator g, such as summation is applied to the input values and the identity information. In this way, the mapping c is invariant to permutations of elements of inputs and the inputs can have arbitrary length. Finally, the fixed-size code c is fed into an ordinary amortized inference net, that transforms the code into statistics of Gaussian distribution to approximate $p(z|x_o)$. Moreover, the previous setting is generalised by iteratively reusing the code c to enlarge the capacity of the neural network. FIG. 9 shows the mechanism of the Partial VAE with iterative point net with two iterations. The mapping c is concatenated back to the input and the same mechanism is performed again.

In some examples, each input variable x may be first input to a respective neural network (or other machine learning system) subsequent to being input to the inference model. The neural networks are symmetric operators (e.g. summation, multiplication, etc.) that take in an input value (of a response) and a respective identifier (of the question responded to) and output an internal vector that is a function of the value and identifier. For example, if the response to question 1 is a score from 1 to 5, the response (e.g. 3) may be concatenated with the question ID (1).

Alternatively, each response and question ID may be input to a single neural network to generate the internal vector. Either way, the outputs of the model $q(z|x_o)$ are a function of the internal vector. For example, the mean and standard variation of the latent space variables z are functions of the user's responses and the questions responded to. This means that the order in which the questions are posed to the user is not important. The questions can be asked in a different order and the same information is obtained.

Reward Function

The model (i.e. the machine learning algorithm) may also predict which question to ask the user next. We want to measure how much our belief in a measure of interest changes with each question that is answered next. That is, we want to measure how much new information we gain for each particular question that is asked.

The reward function is defined as:

$$R_y(i,x_o) = E_{x_i \sim p(x_i|x_o)}[KL(p(y|x_i,x_o) \| p(y|x_o))]$$

where y is the statistic of interest (e.g. a health condition), $x_o$ is the set of answered questions so far, and $x_i$ is the next question to ask out of the set of unanswered questions $x_u$. KL is the Kullback-Leibler divergence and $E_{x_i}$ is the expectation value. The Kullback-Leibler divergence is a measure of how one probability distribution is different from a second, reference probability distribution. The next question to ask $x_i$ is chosen such that $R_y(i,x_o)$ is maximised.

Figure 8:
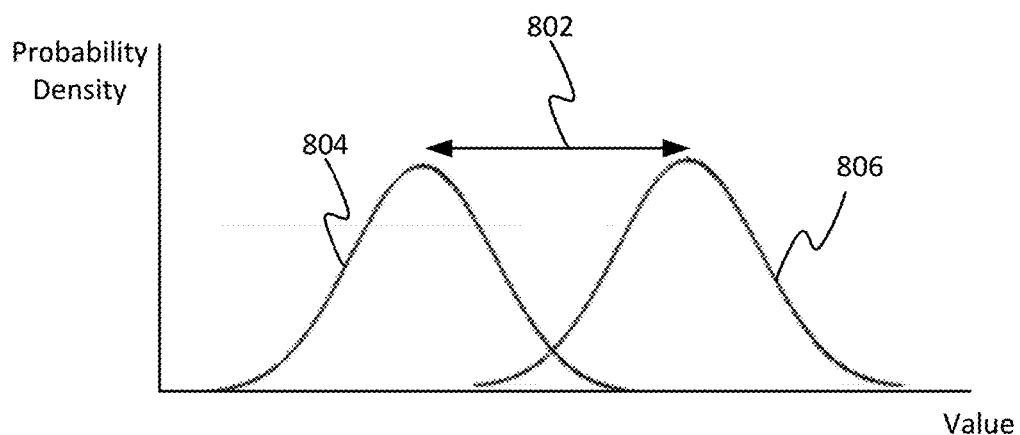
FIG. 8 is a schematic representation of an example reward function.

$p(y|x_i, x_o)$ and $p(y|x_o)$ are densities, or probability distributions. The model optimises the reward function by measuring the distance between the reference distribution $p(y|x_o)$ and each distribution $p(y|x_i, x_o)$ for each question $x_i$. The question that results in the largest shift between those distributions is selected to be output next to the user. The distance or shift between each distribution represents the relative amount of information that would be obtained about the statistic of interest y if question $x_i$ is asked next. FIG. 8 illustrates an example shift 802 between distributions $p(y|x_i, x_o)$ 804 and $p(y|x_o)$ 806.

$R_y(i,x_o)$ is intractable to evaluate given only samples from each of the two distributions because it is a high dimensional integral and has no closed form solution. Therefore the equation needs to be approximated.

Under certain variational distribution families of $q(z|x_o)$ such as, for example, Guassian distributions (commonly used in VAEs), the model always admits analytic solutions of KL-divergences. Therefore instead of calculating the information reward in observational space, the calculations can be performed in latent space:

$$R(i, x_o) = E_{x_i \sim p(x_i|x_o)}[KL(q(z|x_i, x_o) \| q(z|x_o))] -$$
$$E_{x_y,x_i \sim p(x_y, x_i|x_o)}[KL(p(z|x_y, x_i, x_o) \| p(z|x_y, x_o))]$$

Where:

$$p(z|x_y, x_i, x_o) = \frac{p(z|x_i, x_o)p(x_y|z)}{p(x_y|x_i, x_o)}$$

The following approximation may be used:

$$p(z|x_y,x_i,x_o) = q(z|x_y,x_i,x_o)$$

This approximation is computationally efficient since one set of samples $x_y$, $x_i \sim p(x_y, x_i|x_o)$ can be shared across different terms, and KL-divergence between Guassians can be computed exactly without approximate integrals.

The model may therefore output the next question to be asked to the user that maximises the amount of information gained from the user about a particular statistic. For example, the model my select which of a particular set of questions to ask based on the answers to previously posed questions. That is, the machine learning algorithm optimizes the reward function in order to select the optimal question to ask next. Additionally or alternatively, the model may select a time and/or location at which the next question (e.g. out of pre-determined order of questions) is output to the user, as will be discussed below.

Metadata

The items of metadata associated with each question output to the user can be used to adapt the output of future questions to the user.

One of the items of metadata may be a time at which a question is output to the user via the user device. For example, the time may be a time of day, week, month or year. The time may be an absolute time, e.g. 09:30 or a relative time, e.g. an amount of time since the previous question was asked. As another example, the time may be defined as morning, afternoon and evening.

Each input value, e.g. a response (or lack of response) to a question, may be indexed with a metadata value (e.g. a time). For example, if there are 10 questions in total, the set of questions x would contain a question for each unit of time. Taking the example of time being discretised into morning, afternoon and evening, there would 30 questions in the set of questions. The set of questions x may have more elements, each representing a question asked at a different time, or instead the set of questions may be a matrix (e.g. a row of questions, each row of questions having columns of metadata values).

The set of responses and their respective identifiers are fed into the model. The next question to ask is again the question that optimises the reward function (i.e. the question that causes the greatest shift in distributions), but now it is the question having a time that maximises the reward function. The question may then be output at this time. This may mean that the user is more likely to respond at this time. The model may therefore predict which questions the user will answer at which time.

Alternatively or additionally, one of the items of metadata may be the location of the user device when the question is output to the user. Each question is indexed with a location of the user device. The next question to be output to the user is the question having a location that optimises the reward function. The next question is therefore output at this location to maximise the likelihood of the user responding to the question.

In the case where the metadata associated with each question comprises multiple items of metadata (e.g. time and location, or time and facial expression, etc.), note that the "value" of the metadata (as a whole) comprises a vector of constituent values evaluating each of the individual items of metadata.

This technique works equally for other items of metadata. For example, each question may be indexed with one or more of the following items of metadata: a pattern of motion of the user when the questions are asked, an activity being conducted by the user when the questions are asked, a cause which prompted the question to be asked, a sleep pattern of the user around the times the questions are asked, and/or one or more physical conditions or attributes of the user when the questions are asked. The one or more physical conditions of the user may be, for example, a facial expression of the user when the questions are asked, a change in heart rate when the questions are asked, a change in cadence of speech when responding through a voice interface, a change in intonation when responding through a voice interface, a change in cadence of typing when responding in a chat-bot user interface, and/or a change in sentiment when responding in a chat-bot user interface.

As an example, the model may also write the question itself. In this case, $x_i$ becomes the sentence to ask and i is a space over which the model can ask the user any question. The model may use natural language techniques to generate a bespoke question.

Cost

The model may select the next question to ask based on a cost to the user. Each question is assigned a respective cost. The costs may be, for example, a time taken to answer a question, or a cognitive load. Some costs may be dependent on previous questions such that the cost of the next question may grow sequentially. For example, related questions may have a greater cost (e.g. because the user becomes bored of answering similar questions), or they may have a lower cost (e.g. because the user can focus on one train of thought).

The reward function may comprise a cost function. For example, the reward function may be divided by a cost function $C(i, x_o)$. The reward function may be optimised by selecting the next question that maximises the amount of information per unit cost.

Optionally, the model may apply constraints that the next question to be selected must satisfy. For example, a constraint may be that the next question must be answerable in a given amount of time (e.g. three minutes). The next question to be selected is a question that both optimizes the reward function and can be answered within three minutes. The user may provide, as input to the user device, an amount of time that they have available for answering a question. As another example, a constraint may be that the next question must be related to the previous question, or unrelated to the previous question (e.g. no more than four related questions can be asked in a row).

As a further option, the rate at which questions are output to the user via the user device may be adapted (i.e. throttled) in order to meet a constraint. For example, the questions may be output at a rate in order to maintain a level of engagement from the user above a predetermined minimum level.

Visual Representation

Figure 10:
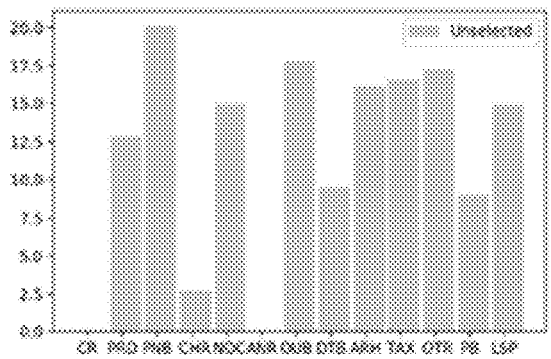
Figure 10:
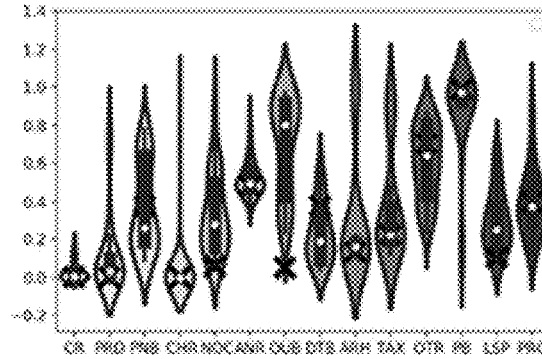
Figure 10:
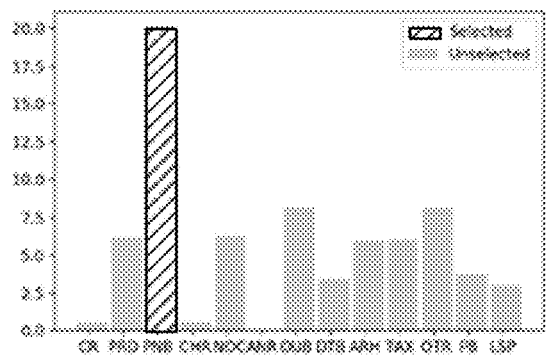
Figure 10:
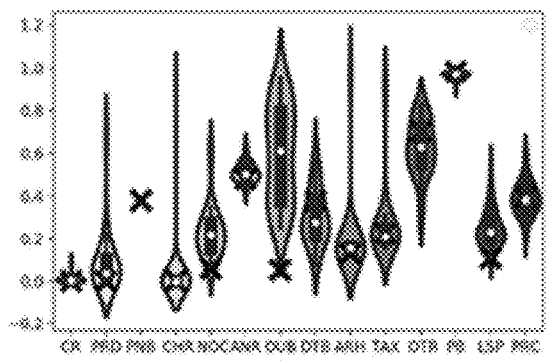
Figure 10:
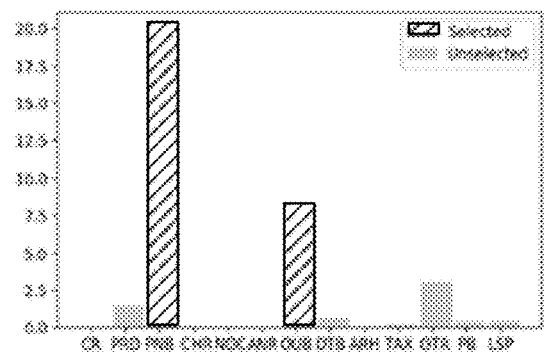
Figure 10:
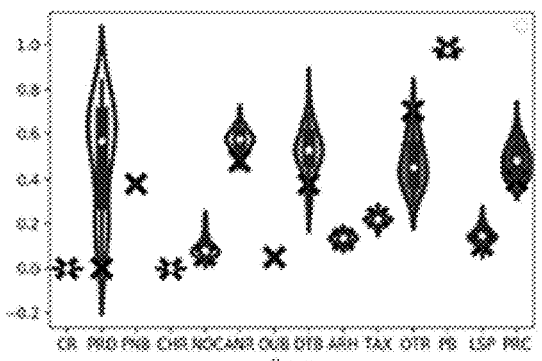
Figure 10:
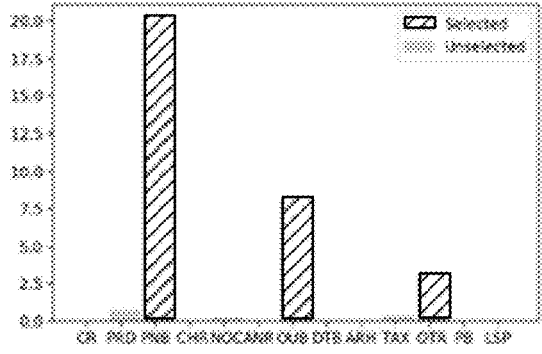
Figure 10:
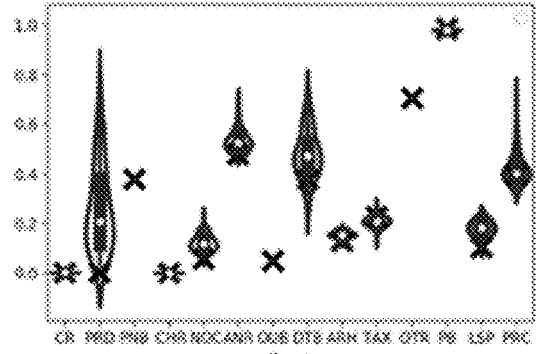

FIG. 10 illustrates how the next question to output to the user is selected. FIGS. 10a, c, e and g are bar charts showing the relative amounts of information content gained (y-axis) if a question is asked on a particular topic (x-axis). For example, if the PNB question is asked (and responded to), 20 units of information content are gained, whilst if the DTB question is asked only 10 units of information content are gained. FIGS. 10b, d, f and h are violin plots showing the current estimate of a response (y-axis) to the questions on the same topics of the bar charts. The outer shape of each "violin" represents all possible results, with the thickness of the violin indicating how common the result it (i.e. the mode result). The central dot represent the median result. FIGS. 10b, d, f and h include one topic, PRC, on the x-axis that FIGS. 10a, c, e and g. This is the hidden variable.

In the examples of FIG. 10, PRC represents the price of a house. The questions are related to variables that can be used to estimate the price of a house. For example, PNB may be a question on the price of other houses in the neighborhood. In the example of FIG. 10, the value of each variable is known and has been plotted as a cross to indicate how the disclosed method converges on the true values.

Each bar of the bar charts represent a question that can be asked to the user. Time flows from top to bottom in FIG. 10. FIG. 10b shows the current estimate of the variables, including the hidden variable PRC, at t0. The relative amount of information content of each bar has been determined by the reward function (i.e. by measuring the distance between the probability distribution of each unanswered question and the probability distribution based on the answered questions). The question with the greatest amount of information to gain from is selected to be output to the user.

FIGS. 10c and d are snapshots taken at time t1. FIG. 10c shows how the amount of information content to be gained from each unanswered question changes as a question is answered. FIG. 10d shows how the estimate of each value has changed now that an additional answer (i.e. the answer to PNB) is known. The estimate of the house price has become more accurate, as shown by the smaller length of the PRC violin.

FIGS. 10e and f and 10g and h show how the amount of information content and estimates of the responses change at t2 and t3 respectively, i.e. as more questions are selected and answered. In these examples, the next question selected is always the question that reveals the most information content.

The amount of information content of a question may be based on the time and/or location at which the question is asked. For example, each question may be split into sub-questions. E.g. the PNB question could be asked in the morning, afternoon, or evening. The amount of information content gained may vary with time. Similarly, the amount of information gained from the other questions may vary with time. It may be the case that the question that reveals the most amount of information at t0 is not PNB—a different question asked at that time may reveal more information.

It will be appreciated that the above embodiments have been described by way of example only.

More generally, according to one aspect disclosed herein, there is provided a computing apparatus comprising one or more processors and storage storing code arranged to run on the one or more processors, wherein the code is configured so as when run to perform operations of: outputting questions to a user via one or more user devices, and receiving back responses to some of the questions from the user via one or more user devices; over time, controlling the outputting of the questions so as to output the questions under circumstances of different values for each of one or more items of metadata, wherein the one or more items of metadata comprise one or more physical conditions of the user; monitoring whether or not the user responds when the question is output with the different metadata values; supplying the metadata values and a corresponding indication of whether the user responded as training inputs to a machine learning algorithm; training the machine learning algorithm to learn a value of each of the one or more items of metadata which optimizes a reward function, and based thereon selecting a circumstance when the user is exhibiting a particular physical condition to output one or more subsequent questions.

In embodiments, said machine learning algorithm may comprise a first neural network and a second neural network, wherein said training comprises: inputting a vector comprising input values to the first neural network in order to generate a respective set of first values from each set of input values, each set of first values representing a probability distribution of a respective one of the input values, and each input value corresponding to a different respective combination of question and associated value of the metadata, wherein each input value represents either the user's response to the respective question under circumstances of the respective metadata or the fact that the user did not respond to the respective question under circumstances of the respective metadata; inputting some or all of the one or more sets of first values to the second neural network in order to generate a respective set of second values from each first set input to the second neural network, each set of second values representing a probability distribution of a respective combination of a predicted response to the respective question under circumstances of its associated metadata; supplying the one or more sets of second values to the reward function to perform said optimization, wherein said reward function comprises an expectation of a distance between (a) each respective probability distribution of the predicted responses and associated metadata of the question not responded to by the user, and (b) an overall probability distribution combining the predicted responses to questions and associated metadata of the questions that have been responded to by the user, and wherein said optimization comprises, for a subsequent question to be output to the user, selecting the metadata value that maximizes said distance between a probability distribution of the predicted response to a question with that metadata value.

In embodiments, said selecting may comprise selecting both which question is to be the subsequent question and the value of its associated metadata, by selecting a combination of subsequent question and associated metadata value that maximizes said distance.

In embodiments, each input value of the vector input to first neural network may be a respective sub-vector of that vector, wherein each sub-vector is generated by inputting the respective input value and a respective identifier of the respective question into a third neural network that performs a symmetric operation on the respective combination of input value and question identifier.

In embodiments, said selecting the circumstance when the user is exhibiting a particular physical condition at which to output the one or more subsequent questions may comprise selecting the circumstance when the user is exhibiting a particular physical condition at which to output the question that maximises the reward function.

In embodiments, each question may be associated with an estimate of cost to the user, and wherein the next one of the one or more subsequent questions selected to be output to the user is the question that maximises an amount of information content gained per unit cost to the user.

In embodiments, the one or more subsequent questions may be output at a rate based on the learned values of each of the one or more items of metadata.

In embodiments, the reward function may comprise a measure of responsivity of the user, and wherein optimizing the reward function comprises increasing the measure of responsivity of the user.

In embodiments, the measure of responsivity of the user may comprise at least one of: (a) a number of responses from the user per unit time, (b) a number of responses per question asked, and (c) an engagement with the question from the user.

In embodiments, the code may be further configured to supply the responses to a scoring algorithm to generate scores predicting a condition of the user based on the responses.

In embodiments, the reward function may comprise a measure of prediction quality, and wherein said optimization comprises optimizing a trade-off between the measure of responsivity and the prediction quality based on the generated scores.

In embodiments, the measure of prediction quality may comprise on at least one of: a statistical uncertainty or variability in the scores, or a comparison with subsequently obtained empirical information on the condition of the user.

In embodiments, the questions may relate to a health condition of the user.

In embodiments, the questions may relate to a health condition of the user, and the predicted condition may comprise the health condition.

In embodiments, the one or more physical conditions of the user may comprise one or more of: a pattern of motion of the user when the questions are asked, an activity being conducted by the user when the questions are asked, a cause which prompted the question to be asked, a sleep pattern of the user around the times the questions are asked, a facial expression of the user when the questions are asked, a change in heart rate when the questions are asked, a change in cadence of speech when responding through a voice interface, a change in intonation when responding through a voice interface, a change in cadence of typing when responding in a chat-bot user interface, and/or a change in sentiment when responding in a chat-bot user interface.

In embodiments, the one or more items of metadata may comprise one or more controllable parameters of the questions or a manner in which the questions are output, wherein the one or more controllable parameters comprise one of more of: a frequency at which the questions are asked, a time and/or location at which the questions are asked, how many questions are asked per sitting, which user device is used to ask the questions, whether the questions are output audibly or visually, and/or a type of user interface used to output the questions.

In embodiments, the one or more items of metadata may be a plurality of items of metadata, and said training may comprise training the machine learning algorithm to learn a combination of the metadata values that optimizes said reward function.

In embodiments, the questions output under circumstances of the different values of a given one of the items of metadata may comprise: some repeated instances of the same question, and some different questions.

According to another aspect disclosed herein, there is provided a computer program embodied on computer-readable storage and configured so as when run one or more processors to perform operations of: outputting questions to a user via one or more user devices, and receiving back responses to some of the questions from the user via one or more user devices; over time, controlling the outputting of the questions so as to output the questions under circumstances of different values for each of one or more items of metadata, wherein the one or more items of metadata comprise one or more physical conditions of the user; monitoring whether or not the user responds when the question is output with the different metadata values; supplying the metadata values and a corresponding indication of whether the user responded as training inputs to a machine learning algorithm; training the machine learning algorithm to learn a value of each of the one or more items of metadata which optimizes a reward function, and based thereon selecting a circumstance when the user is exhibiting a particular physical condition to output one or more subsequent questions.

According to another aspect disclosed herein, there is provided a computer-implemented method comprising: outputting questions to a user via one or more user devices, and receiving back responses to some of the questions from the user via one or more user devices; over time, controlling the outputting of the questions so as to output the questions under circumstances of different values for each of one or more items of metadata, wherein the one or more items of metadata comprise one or more physical conditions of the user; monitoring whether or not the user responds when the question is output with the different metadata values; training the machine learning algorithm to learn a value of each of the one or more items of metadata which optimizes a reward function, and based thereon selecting a circumstance when the user is exhibiting a particular physical condition to output one or more subsequent questions.

Other variants or applications may become apparent to a person skilled in the art once given the disclosure herein. The scope of the disclosure is not limited by the above-described embodiments but only by the accompanying claims.

The invention claimed is:

1. A computing apparatus comprising a processor and storage storing code arranged to run on the processor, wherein the code is configured so as when run to perform operations of:
 outputting questions to a user via a user device, and receiving back responses to some of the questions from the user via the user device;
 controlling the outputting of the questions so as to output the questions with a different value associated with each item of a plurality of items of metadata, wherein the items of metadata comprise a physical condition of the user;
 determining a probability distribution of an unanswered question of the questions; and
 training a machine learning algorithm to learn a value of each of the items of metadata which optimizes a reward function based on the determined probability distribution, and based thereon selecting a circumstance when the user is exhibiting a particular physical condition to output a subsequent question, wherein the reward function comprises a distance between the probability distribution of the unanswered question and a probability distribution based on an answered question of the questions.

2. The apparatus according to claim 1, wherein said machine learning algorithm comprises a first neural network and a second neural network, wherein said training comprises:
 inputting a vector comprising input values to the first neural network in order to generate a respective set of first values from each set of input values, each set of first values representing a probability distribution of a respective one of the input values, and each input value corresponding to a different respective combination of a question and associated value of the metadata, wherein each input value represents either the user's response to the respective question under circumstances of the respective metadata or that the user did not respond to the respective question under circumstances of the respective metadata;
 inputting some or all of the sets of first values to the second neural network in order to generate a respective set of second values from each first set input to the second neural network, each set of second values representing a probability distribution of a respective combination of a predicted response to the respective question under circumstances of its associated metadata; and
 supplying the sets of second values to the reward function to perform said optimization, wherein said reward function comprises an expectation of a distance between (a) each respective probability distribution of the predicted responses and associated metadata of the question not responded to by the user, and (b) an overall probability distribution combining the predicted responses to questions and associated metadata of the questions that have been responded to by the user, wherein said optimization comprises, for a subsequent question to be output to the user, selecting the metadata value that maximizes said distance between a probability distribution of the predicted response to a question with that metadata value.

3. The apparatus according to claim 2, wherein said selecting comprises selecting both which question is to be the subsequent question and the value of its associated metadata, by selecting a combination of subsequent question and associated metadata value that maximizes said distance.

4. The apparatus according to claim 2, wherein each input value of the vector input to first neural network is a respective sub-vector of that vector, wherein each sub-vector is generated by inputting the respective input value and a respective identifier of the respective question into a third neural network that performs a symmetric operation on the respective combination of input value and question identifier.

5. The apparatus according to claim 1, wherein said selecting the circumstance when the user is exhibiting a particular physical condition at which to output the subsequent question comprises selecting the circumstance when the user is exhibiting a particular physical condition at which to output the question that maximises the reward function.

6. The apparatus according to claim 1, wherein each question is associated with an estimate of cost to the user, and wherein a next one of the subsequent question selected to be output to the user is the question that maximises an amount of information content gained per unit cost to the user.

7. The apparatus according to claim 1, wherein the reward function comprises a measure of responsivity of the user, and wherein optimizing the reward function comprises increasing the measure of responsivity of the user.

8. The apparatus according to claim 7, wherein the measure of responsivity of the user comprises at least one of: (a) a number of responses from the user per unit time, (b) a number of responses per question asked, and (c) an engagement with the question from the user.

9. The apparatus according to claim 1, wherein the code is further configured to supply the responses to a scoring algorithm to generate scores predicting a condition of the user based on the responses.

10. The apparatus according to claim 9, wherein the reward function comprises a measure of prediction quality, and wherein said optimization comprises optimizing a trade-off between a measure of responsivity and the measure of prediction quality based on the generated scores.

11. The apparatus according to claim 10, wherein the measure of prediction quality comprises at least one of:
 a statistical uncertainty or variability in the scores, or
 a comparison with subsequently obtained empirical information on the condition of the user.

12. The apparatus according to claim 9, wherein the questions relate to a health condition of the user, and the predicted condition comprises the health condition.

13. The apparatus according to claim 1, wherein the physical condition of the user comprises one or more of:
 a pattern of motion of the user when the questions are asked,
 an activity being conducted by the user when the questions are asked,
 a cause which prompted one or more of the questions to be asked,
 a sleep pattern of the user around the times the questions are asked,
 a facial expression of the user when the questions are asked,
 a change in heart rate when the questions are asked, a change in cadence of speech when responding through a voice interface,
a change in intonation when responding through a voice interface,
a change in cadence of typing when responding in a chat-bot user interface, and/or
a change in sentiment when responding in a chat-bot user interface.

14. The apparatus according to claim 1, wherein the items of metadata comprise a controllable parameter of the questions or a manner in which the questions are output, wherein the controllable parameter comprises one or more of:
a frequency at which the questions are asked,
how many questions are asked per sitting,
which user device is used to ask the questions,
whether the questions are output audibly or visually,
a type of user interface used to output the questions.

15. The apparatus according to claim 1, wherein said training comprises training the machine learning algorithm to learn a combination of the metadata values that optimizes said reward function.

16. The apparatus according to claim 1, wherein the questions output under circumstances of the different values of a given one of the items of metadata comprise: some repeated instances of a same question, and some different questions.

17. The apparatus according to claim 1, wherein training the machine learning algorithm comprises, for a subsequent question to be output to the user, selecting the value that maximizes the distance between the probability distribution of the unanswered question and the probability distribution based on the answered question of the questions.

18. A computing device having a computer program embodied on computer-readable memory and configured so as when run a processor performs operations of:
outputting questions to a user via a user device, and receiving back responses to some of the questions from the user via the user device;
controlling the outputting of the questions so as to output the questions with a different value associated with each item of a plurality of items of metadata, wherein the items of metadata comprise a physical condition of the user;
determining a probability distribution of an unanswered question of the questions; and training a machine learning algorithm to learn a value of each of the items of metadata which optimizes a reward function based on the determined probability distribution, and based thereon selecting a circumstance when the user is exhibiting a particular physical condition to output a subsequent question, wherein the reward function comprises a distance between the probability distribution of the unanswered question and a probability distribution based on an answered question of the questions.

19. The computing device according to claim 18, wherein training the machine learning algorithm comprises, for a subsequent question to be output to the user, selecting the value that maximizes the distance between the probability distribution of the unanswered question and the probability distribution based on the answered question of the questions.

20. A computer-implemented method comprising:
outputting questions to a user via a user device, and receiving back responses to some of the questions from the user via the user device;
controlling the outputting of the questions so as to output the questions with a different value associated with each item of a plurality of items of metadata, wherein the items of metadata comprise a physical condition of the user;
determining a probability distribution of an unanswered question of the questions; and
training a machine learning algorithm to learn a value of each of the items of metadata which optimizes a reward function based on the determined probability distribution, and based thereon selecting a circumstance when the user is exhibiting a particular physical condition to output a subsequent question, wherein the reward function comprises a distance between the probability distribution of the unanswered question and a probability distribution based on an answered question of the questions.

* * * * *